United States Patent [19]
Nagai et al.

[11] Patent Number: 6,010,883
[45] Date of Patent: Jan. 4, 2000

[54] RECOMBINANT FUSION PROTEINS

[75] Inventors: Kiyoshi Nagai, Cambridge; Hans Christian Thøgersen, Sawston, both of United Kingdom

[73] Assignee: Celltech Therapeutics Limited, Slough, United Kingdom

[21] Appl. No.: 07/854,749

[22] Filed: Mar. 19, 1992

Related U.S. Application Data

[63] Continuation of application No. 07/337,050, Apr. 12, 1989, abandoned, which is a continuation of application No. 06/733,691, May 13, 1985, abandoned.

[30] Foreign Application Priority Data

May 16, 1984 [GB] United Kingdom .................... 8412517

[51] Int. Cl.$^7$ ........................... C12N 15/62; C12N 15/74; C12N 15/12; C12N 15/13; C12N 15/14
[52] U.S. Cl. ...................... 435/69.7; 435/69.1; 435/69.4; 435/69.6; 435/71.1; 435/252.3; 435/320.1; 435/471; 536/23.4; 536/23.5; 536/23.51; 536/23.53
[58] Field of Search .................... 536/23.4, 23.5, 536/23.51, 23.53; 435/69.1, 69.4, 69.6, 69.7, 41.1, 252.3, 320.1, 471

[56] References Cited

U.S. PATENT DOCUMENTS

| | | | |
|---|---|---|---|
| 4,366,246 | 12/1982 | Riggs | 435/68 |
| 4,532,207 | 7/1985 | Brewer et al. | 435/68 |
| 4,543,329 | 9/1985 | Daum et al. | 435/69 |

FOREIGN PATENT DOCUMENTS

| | | | |
|---|---|---|---|
| 0035384 | 9/1981 | European Pat. Off. | ......... C12N 15/00 |
| 35384 | 9/1981 | European Pat. Off. . | |
| 2121054 | 12/1983 | United Kingdom . | |
| 2140810 | 12/1984 | United Kingdom . | |
| 2142337 | 1/1985 | United Kingdom . | |
| 2160206 | 12/1985 | United Kingdom . | |

| | | | |
|---|---|---|---|
| WO8401173 | 3/1984 | WIPO . | |
| WO84/02351 | 6/1984 | WIPO | ............................. C12P 21/06 |
| WO8403103 | 8/1984 | WIPO . | |

OTHER PUBLICATIONS

Biological Abstracts, 63, 3, 1270, No. 12884 (1977).
Biological Abstracts, 74, 11, 7609, No. 73568 (1982).
Nagai, *Nature*, 309, 5971, pp. 810–812 (1984).
Sassenfeld et al., Bio/Technology, 2, 76–81 (1984).
"Protein Purification from Molecular Mechanisms to Large–Scale Processes," American Chemical Society, Washington, D.C. (1990), Chapter 13, pp. 181–193.
"Factor Xa for Recombinant Peptide Production —Specific Cleavage Releases Desired Product from Fusion Proteins" InFerGene COmpany, Benicia, California.
Aurell et al. 1977. Thrombosis Res. 11: 595–609.
Fujikawa et al. 1972. Biochem. 11(26): 4882–4891.
Degen et al. 1983. Biochem. 22: 2087–2097.
Herrera–Estrella et al. 1983. Nature 303: 209–213.

*Primary Examiner*—David T. Fox
*Attorney, Agent, or Firm*—Venable; John W. Schneller

[57] ABSTRACT

This invention provides a DNA sequence coding for a cleavage site which is specifically cleaved by blood coagulation Factor Xa, a vector containing such a sequence, and a host organism transformed with such a vector. Preferably, in the vector, the Factor Xa cleavage site coding sequence is fused at one end to a product and at its other end to an ATG codon or a sequence coding for at least part of a host protein.

This invention also provides a process, for the production of a desired protein or peptide product in native form, comprising:

transforming a host organism with a vector as described above;

expressing the desired protein or peptide product as a fusion protein comprising the desired protein or peptide product fused to a Factor Xa cleavage site; and a cleaving the fusion protein with Factor Xa to yield the foreign gene product in native form.

23 Claims, 3 Drawing Sheets

RECOMBINANT FUSION PROTEINS

This application is a continuation of application Ser. No. 07/337,050, filed Apr. 12th, 1989, now abandoned, which is a continuation of application Ser. No. 06/733,691 filed May 13th, 1985, now abandoned.

FIELD OF THE INVENTION

This invention relates to recombinant DNA technology and in particular to recombinant fusion proteins and to methods of cleaving such fusion proteins to yield foreign gene products in native form.

TECHNOLOGY BACKGROUND

In recent years, developments in recombinant DNA technology have made it possible to express a wide range of cloned foreign genes in host organisms such as bacteria and yeasts. Two main approaches have been employed.

In one approach, expression of the foreign gene has been placed under the direct control of host expression control sequences, e.g. an E. coli promoter and Shine-Delgarno sequence, to yield non-fused foreign protein and polypeptide products. However this approach has various shortcomings.

High level expression in $E.\ coli$ of many eucaryotic genes has proved difficult even when a strong promoter, such as the $E.\ coli$ $\lambda$ $P_L$ or Trp promoter and the Shine-Delgarno sequence from a highly expressed $E.\ coli$ gene have been used in front of the foreign gene sequence. These difficulties apparently arise because the secondary structure of the mRNA in the vicinity of the Shine-Delgarno sequence affects the accessibility of mRNA to the ribosome and consequently the translational efficiency. Since the secondary structure depends on the sequence which follows the initiation codon, i.e. the foreign gene sequence, such constructions often result in poor translational efficiency.

Also many proteins expressed in $E.\ coli$ have an extra methionine amino acid residue at their N-terminus, arising from the ATG initiaton codon at the 5' end of the foreign gene which is required to initiate translation. The presence of this extra N-terminal methionine is undesirable as it may affect the stability and activity of the protein and, if the protein is to be used clinically, may cause antigenicity problems.

Furthermore, directly expressed foreign gene products, in particular when they are relatively small polypeptides such as some hormones, are often subject to proteolytic turnover within the host organism cells. The leads to very low levels of accumulation of the foreign gene product within the host cells.

In an alternative approach, many eucaryotic proteins have been produced in large amount in $E.\ coli$ in the form of hybrid fusion proteins obtained by fusing the foreign gene sequence to the coding sequence of a highly expressed $E.\ coli$ gene, such as the lacZ, tufB, bla, $\lambda$CII and $\lambda$N genes. In such constructions, run-on of translation from the bacterial gene provides high translational efficiency. Furthermore, the presence of bacterial protein fused to the foreign gene product may render the fusion protein resistant to proteolytic turnover and may also provide for compartmentalisation of the fusion protein within the host cells or its secretion therefrom. Also by fusion protein expression, potentially biohazardous materials such as peptide hormones may be produced in an inactive 'pro-form' which may then be activated subsequently in vitro by specific cleavage.

However such hybrid fusion proteins themselves are not normally suitable as end products, e.g. for clinical use, and it is necessary to cleave specifically the fusion protein to release the foreign gene product in native form. Specific single or double amino acid cleavage sites have been provided within fusion proteins at the junction between the $E.\ coli$ protein and the eucaryotic protein. For instance cyanogen-bromide chemical treatment has been used to cleave at single methionine amino acid cleavage sites and trypsin enzymatic treatment has been used to cleave at single arginine or lysine or double arginine—arginine or lysine—lysine cleavage sites. However, such single or double repeated amino acid cleavage sites are of only limited applicability as, if the cleavage site amino acids are present within the foreign gene product amino acid sequence, cleavage treatment will lead to unwanted cleavage of the foreign protein as well as cleavage at the junction of the fusion protein.

EP-A-0 035 384 (The Regents of the University of California) describes the use of specific cleavage linkers at the junction between host and foreign DNA sequences in the construction of recombinant DNA sequences which code for fusion proteins. These include cleavage linkers which code for extended specific cleavage sequences which comprise a sequence of at least two different amino acids which provide a specific enzyme cleavage site. The greater the number of amino acid residues in the specific cleavage sequence, the smaller is the probability of a similar sequence occurring within the foreign gene product amino acid sequence, and thus the lower is the risk of there being unwanted cleavage of the foreign protein. EP-A-0 035 384 specifically describes the use of a cleavage linker having the sequence X—(Asp)$_n$—Lys—Y, where n=2–4, which is cleaved on the carboxyl side of Lys specifically by enterokinase. However, the cleavage sites described in EP-A-0 035 384 are not completely satisfactory for use in the cleavage of fusion proteins. For instance, it has been shown (Anderson et al, Biochemistry 16, 3354- (1977))that enterokinase cleaves procoocoonase at the peptide bond following the sequence Gly—Glys—Lys, and thus it appears that enterokinase cleavage is not uniquely dependent upon the sequence X—(Asp)$_n$—Lysp—Y.

SUMMARY OF THE INVENTION

We have now devised improved cleavage linkers for use in the construction of recombinant DNA sequences which code for fusion proteins. Each linker codes for an enzyme cleavage site comprising a sequence of 4 different amino acids. These cleavage sequences are rarely found in other protein sequences and thus these cleavage sites will be suitable for use in the cleavage of a very wide range of recombinant fusion proteins. Furthermore, it appears that cleavage by the enzyme at these sites is not dependent upon overall three dimensional protein structure, as may be the case with other extended specific cleavage sequences, such as those which have been proposed previously, but is strictly sequence specific.

Accordingly, the present invention provides a DNA sequence coding for a cleavage site which is specifically cleaved by blood coagulation factor $X_a$.

The invention also includes a vector comprising a DNA sequence coding for a cleavage site which is specifically cleaved by blood coagulation factor $X_a$ and host organisms transformed with such a vector.

Furthermore the invention includes a process for the production of a foreign gene product in native form in which host organisms are transformed with a vector comprising DNA sequences coding for the foreign gene product and at least one cleavage site which is specifically cleaved by blood coagulation factor $X_a$, the foreign gene product is expressed as a fusion protein by the transformed organisms and the fusion protein is cleaved by treatment with activated blood coagulation factor X to yield the foreign gene product in native form.

In the present description the phrase 'in native form' refers to a polypeptide or protein comprising the amino acid sequence thereof without additional amino acid residues, e.g. additional N-terminal amino acid residues such as an N-terminal methionine amino acid residue or N-terminal host protein amino acid residues.

Also in the present description the term blood coagulation factor $X_a$ refers to any activated blood coagulation factor X including factor $X_a$ derived from any mammalian or recombinant source. In particular these include bovine factor $X_{1a}$ and bovine factor $X_{2a}$.

Blood coagulation factor X is the proenzyme of a serine protease, factor $X_a$ (E.C.3.4.21.6), which activates prothrombin to thrombin by specific limited proteolysis at the bonds, Arg (274) —Thr (275) and Arg (323) —Ile (324). In prothrmobin both cleavage sites are preceded by the same tetrapeptide, Ile—Glu—Gly—Arg, which has been proposed as a determinant of factor $X_a$ substrate recognition (Magnusson, S et al, *Proteases and Biological Control* (Eds Reich, E; Rifkin, D B and Shaw, E) 123–149, Cold Spring Harbor Laboratory, New York, 1975). Some of the peptide sequences known to be cleaved by factor $X_a$ are listed in Table 1 below.

Factor $X_a$ cleavage of native prothrombin is identical with cleavage of chymotryptic peptides containing the peptide segments identified in Table 1 (Magnusson et al supra, Magnusson et al, *Proteolysis and Physiological Regulation*, Eds. Ribbons, D W and Brew, K; 203–238, Academic Press, New York 1976).

Work has also been carried out on the production of chromogenic substrates for use in the determination of Factor $X_a$. In this respect, reference may be made to:

"Chromogenic Substrates based on the Primary Structure of Prothrombin-Especially intended for the Determination of Factor $X_a$ activity", Aurell, L, et al., Peptides 1976 (Proceedings of the Fourteenth European Peptide Symposium, Wépion, Belgium, Apr. 11–17, 1976, 191–195, 1976;

"A New Sensitive and Highly Specific Chromogenic Peptide Substrate for Factor $X_a$", Aurell, L, et al., *Thrombosis Research*, 11, 595–609, 1977;

"New chromogenic Peptide Substrates for Factor $X_a$", Aurell, L, et al., *Haemostasis*, 7, 92–94, 1978; and "Small Synthetic Peptides with Affinity for Proteases in Coagulation and Fibrinolysis: An Overview", Claeson, G, and Aurell, L, Annals of the New York Academy of Sciences, 370, 798–811, 1981.

This work has indicated that specific cleavage at an enhanced rate can be obtained if the $P_3$ residue is Gln rather than Glu, and that specific cleavage at a reduced rate can be obtained if the $P_4$ residue is Leu or Pro rather than Ile or the $P_3$ residue is Asn rather than Glu.

Also it has been found that the peptide bond following Ala—Glu—Gly—Arg in a chymotryptic peptide from antithrombin III is also cleaved by factor $X_a$.

It appears, therefore, that the structure required for recognition by factor $X_a$ is determined by the local sequence at the cleavage site. Each of the sequences referred to above contains arginine and glycine at the $P_1$ and $P_2$ sites respectively, and a glutamic or aspartic acid or glutamine or asparagine residue at the $P_3$ site. Isoleucine at the $P_4$ site is conserved in all factor $X_a$ cleavage sites in human and bovine prothrombin but from the other data, it appears that the cleavage requirement may only be for a small hydrophobic residue at the $P_4$ site.

The DNA sequence of the invention may code for any cleavage site which is specifically cleaved by blood coagulation factor $X_a$ including all of the specific factor $X_a$ cleavage sequences discussed above. Preferably the DNA sequence is a sequence coding for the amino acid sequence

TABLE 1

Peptide bonds known to be cleaved by blood coagulation factor $X_a$

| ----$P_4$-$P_3$-$P_2$-$P_1$=$P_1'$-$P_2'$-$P_3'$-$P_4'$---- | Substrate |
|---|---|
| ----Ile-Glu-Gly-Arg=Val-His-Leu-Thr--- | CIIFXβ-globin |
| ----Ile-Glu-Gly-Arg=Thr-Ala-Thr-Ser--- | human prothrombin |
| ----Ile-Glu-Gly-Arg=Thr-Ser-Glu-Asp--- | bovine prothrombin |
| ----Ile-Asp-Gly-Arg=Ile-Val-Glu-Gly--- | human prothrombin |
| ----Ile-Glu-Gly-Arg=Ile-Val-Glu-Gly--- | bovine prothrombin |
| ----Ala-Glu-Gly-Arg=Asp-Asp-Leu-Tyr--- | human antithrombin III |

Proteolytic cleavage by blood coagulation factor $X_a$ takes place between $P_1$ and $P_1'$ sites.

X—Y—Gly—Arg wherein X is Ile, Leu, Pro or Ala, and Y is Glu, Asp, Gln or Asn. More preferably, X is Ile and Y is Glu or Gln. Most preferably the DNA sequence is a sequence coding for the amino acid sequence Ile—Glu—Gly—Arg.

The specific nucleotides present in the DNA will depend upon the particular amino acid sequence of the cleavage site and the genetic code. Thus, in view of the redundancy of the genetic code, a plurality of different DNA sequences may be used to code for a single cleavage site. A particular DNA sequence may be chosen having regard to host codon usage preferences and/or to facilitate DNA manipulations, for instance to provide convenient endonuclease restriction sites. Examples of DNA sequences which code for the Ile—Glu—Gly—Arg cleavage site are

```
ATC GAG GGT AGG
``` and

```
ATT GAA GGT CGT
```

The first sequence mentioned above is particularly useful in that, if the codon CCT is added to it, the restriction site for the endonuclease Stu 1 is formed, cleavage taking place between the AGG and CCT codons.

The vectors of the invention may comprise the DNA sequence coding for the factor $X_a$ cleavage site without associated fusion protein coding sequences, such as the vector M13mp11FX as hereinafter specifically described. Such vectors provide a source of DNA sequence coding for the cleavage site and typically comprise appropriate endonuclease restriction sites to permit excision of the cleavage site coding sequence or cloning of other DNA sequences, e.g. a foreign gene sequence, for construction of fusion protein vectors. For instance, the StuI site of M13mp11FX provides a suitable site for cloning of coding sequences.

Preferably, however, the vectors of the invention comprise fusion protein expression vectors which characteristically contain a foreign gene fused to a DNA sequence coding for a factor $X_a$ cleavage site. Thus the fusion protein may comprise an N-terminal methionine amino acid residue linked via the factor $X_a$ cleavage sequence to a foreign gene product. More usually, however, the fusion protein comprises a host protein sequence fused to a foreign gene product via a factor $X_a$ cleavage sequence, and corresponding vectors comprise host protein coding sequences fused via the Factor $X_a$ cleavage site coding sequence to a foreign protein coding sequence. Typically the host protein and cleavage site amino acid coding sequences are fused to the N-terminus of the foreign protein coding sequence.

It will be appreciated that it may be necessary to add further nucleotide residues to the Factor $X_a$ cleavage sequence in order to bring the foreign protein sequence into the correct reading frame with respect to the initiation codon of the vector.

Expression of proteins in the host cells transformed with fusion protein expression vectors according to the invention leads to the production of fusion proteins comprising at least a desired foreign protein or peptide having linked thereto the Factor $X_a$ cleavage sequence. Generally the fusion protein comprises at least part of a host protein attached to the desired foreign protein or peptide via the Factor $X_a$ cleavage sequence. Fusion proteins which contain a factor $X_a$ cleavage site are included within the scope of the invention.

Any foreign gene product may be produced using the fusion protein expression vectors of the invention. Such products may include eucaryotic, e.g. mammalian, polypeptides and proteins including enzymes, serum proteins, e.g. β-globin, and peptide hormones and precursors thereof, e.g. calcitonin-glycine.

Any suitable host protein or part thereof may be used for fusion protein expression. Examples of suitable bacterial host protein genes include the lacZ, tufB, trpE, trpD, bla, λCII and CAT genes, The invention is widely applicable to the production of recombinant fusion proteins in host organisms in general including yeast and mammalian cells. However the invention is particularly applicable to bacterial host cells including Bacillus host cells or especially *E. coli* host cells. The methods and procedures used for preparation of the DNA sequences of the invention, e.g. oligonucleotide synthesis, the preparation of vectors, transformation of host organisms and expression of fusion proteins are well known in the art of recombinant DNA technology.

In the process of the invention a fusion protein, expressed by host cells transformed with a fusion protein expression vector, is cleaved by treatment with activated factor X to yield the foreign gene product in native form. Any suitable blood coagulation factor $X_a$ may be used, including human factor Xa or, preferably bovine factor $X_a$.

The proenzyme, factor X, may be readily prepared from human, bovine or other mammalian blood plasma. For instance, factor X may be isolated in a biochemically pure form and free from contaminating proteases after adsorption from bovine plasma on insoluble barium salts followed by a chromatographic step (Fujikawa et al, Biochemistry 11, 4882–4891, (1972)). Any suitable activation may be used to convert the proenzyme to its active form, i.e. factor $X_a$, including activation with Russell's viper venom or immobilised trypsin activity. Using factor $X_a$ isolated from bovine plasma at an enzyme to substrate molar ratio of approximately 1:100 it has been found that fusion protein digestion was complete within two hours. Following cleavage, foreign gene products may be recovered and otherwise treated as desired.

Generally it has been found that the amino acid sequence of the foreign gene product does not significantly affect the efficiency of cleavage. However it is believed, in view of results obtained with other serine proteases, that factor $X_a$ will not cleave when a proline amino acid residue follows immediately after the arginine residue of the factor $X_a$ cleavage site.

Treatment with activated factor X cleaves the fusion proteins of the invention preferentially preferably substantially exclusively, at the peptide bond following the arginine amino acid residue of the factor $X_a$ cleavage site to liberate foreign gene product in native form. Thus treatment with activated factor X may be used to cleave an N-terminal methionine amino acid residue or host protein amino acid sequences together with factor $X_a$ cleavage site amino acid sequence from the foreign gene product amino acid sequences.

In certain circumstances, it may be found that the desired foreign protein contains an amino acid sequence which is susceptible to cleavage by Factor Xa. In such cases it may nonetheless be possible to use the process of the invention to obtain the foreign protein. For instance, the susceptible sequence in the foreign protein may be a kinetically less preferred sequence, such as one having Pro instead of Ile at $P_4$, or it may be 'buried' in the foreign protein. In such cases, the rate at which the sequence in the foreign protein is cleaved may be significantly less than that at which the linker sequence is cleaved, and it may therefore prove possible to obtain substantially complete cleavage of the linker sequence without significant cleavage of the sequence in the foreign protein by controlling the reaction conditions or by restricting the time for which cleavage is carried out.

BRIEF DESCRIPTION OF THE DRAWINGS

The invention is further described by way of illustration only in the following examples. It will be appreciated that the invention is not limited to the specific examples described.

DETAILED DESCRIPTION OF THE INVENTION

EXAMPLE 1

Preparation of factor $X_a$ Cleavage Site Coding Sequence and Construction of Vectors A phage vector M13mp11FX containing a DNA sequence coding for the Ile—Glu—Gly—Arg recognition site for factor $X_a$ was constructed. Also two vectors pLcILFXβ and pLcIIβ, which direct efficient production of hybrid fusion proteins comprising the 31 amino-terminal residues of the λCII protein and the complete amino acid sequence of human β-globin, were constructed. The former of these vectors comprises, in addition, a DNA sequence coding for the Ile—Glu—Gly—Arg factor $X_a$ cleavage site linking the λCII and β-globin coding sequences.

METHODS

All DNA manipulations were carried out essentially as described by Maniatis et al, ('Molecular Cloning' Cold Spring Harbor, N.Y., 1982). A temperature sensitive lysogenic strain MZ-1 (gal $K_{am}\Delta 8$ att LΔ Bam $N_7$ $N_{53}$ $_cI857$ ΔH1, his⁻, ilv⁻, bio⁻, N⁺, a gift from Dr K McKenney) was used as a host strain for plasmids containing $\lambda P_L$ promoter. Transformation was carried out by the method of Remaut et al (Gene 15, 81–93 (1981)). T4 DNA ligase was prepared from strain NM 989 (Murray et al, J Molec Biol 132, 493–505 (1979) and Tait et al, 3 Biol Chem 255, 813–815 (1980)). Restriction enzymes were purchased from New England BioLabs.

(a) M13mp11FX

Figure 1:
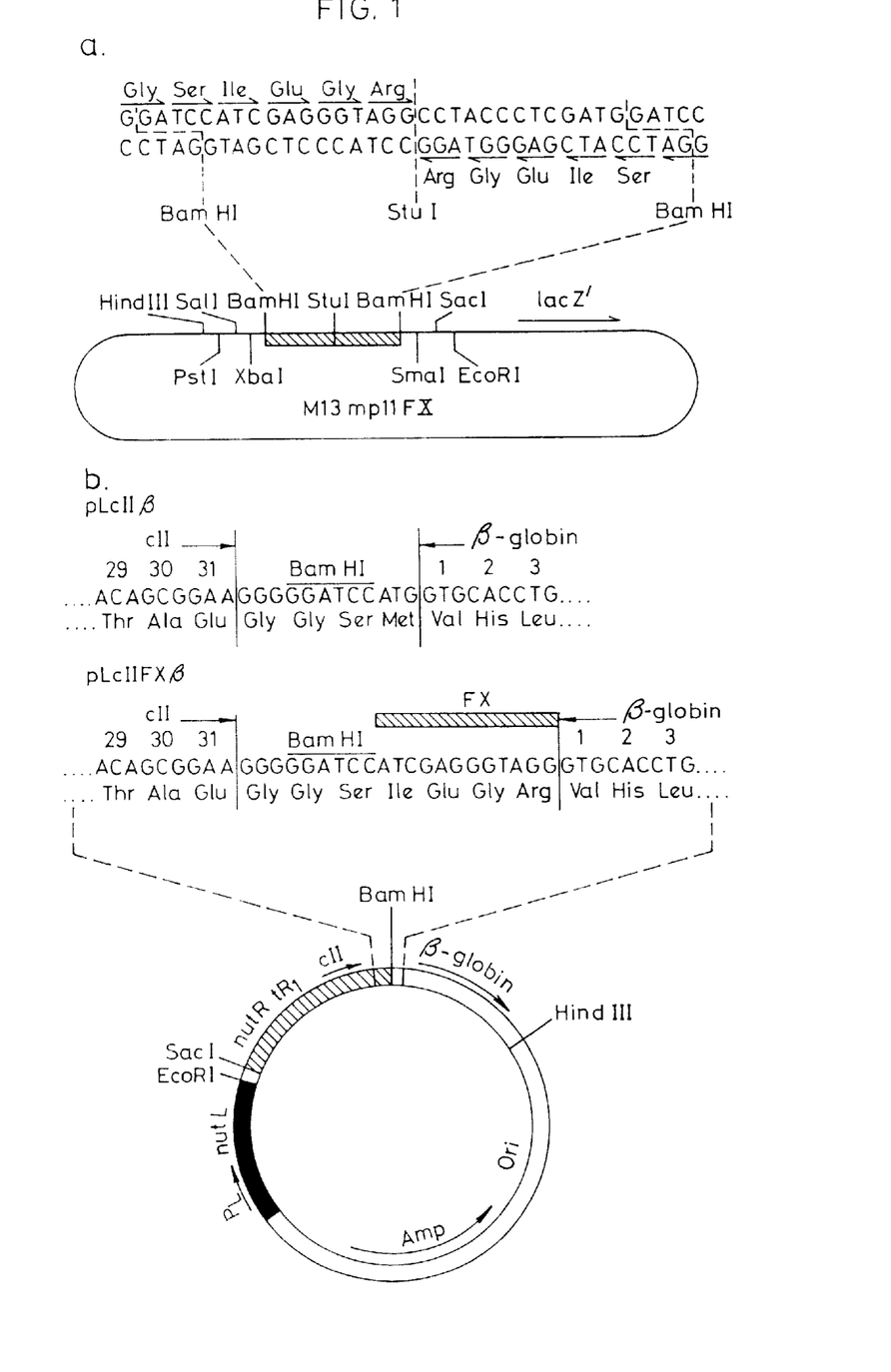
FIG. 1*a* shows DNA sequences and enzyme restriction maps indicating the mode of construction of a vector containing sequence coding for the cleavage site for Factor $X_a$ and FIG. 1*b* shows the construction of vectors encoding fusion proteins with and without the Factor $X_a$ cleavage site inserted between a portion of the CII gene and the β-globin gene.

Two oligonucleotides dTACCCTCGATGGATC and dCATCGAGGGTAGGCC were synthesised by the phosphotriester method on a controlled pore glass support (Sproat et al, Tetrahedron Lett, 24, 5771–5774, (1983)) and purified by HPLC (Gait et al, Nucleic Acids Research, 10, 6243–6254 (1982). The two oligonucleotides were allowed to anneal after phosphorylation with T4 polynucleotide kinase (P-L Biochemicals) and r[$\gamma^{-32P}$] ATP (3,000 Ci/m mol, Amersham) and ligated to form concatamers. The DNA was then digested with BamHI and cloned into the dephosphorylated site of M13mp11 (Vieira et al, Gene 19, 259–268 (1982)) to yield M13mp11FX as shown in FIG. 1. This vector forms blue plaques in the presence of isopropyl-β-D-thiogalacto-pyranoside and 5-bromo-4-chloro-3-indolyl-β-d-galactoside (Sigma).

(b) pLcIIβ and pLcIIFXβ

The Eco R1-HindIII fragment containing the multi-restriction sites was cut out from M13mp10 (Vieira et al supra) and ligated to EcoR1-HindIII cut pLc245 (Remaut et al, supra) to form pLmp10. The 319 bp AluI fragment containing the nutR, $t_{R1}$ sites and a part of the CII gene was cut out from pKG1805 (McKenney, K, PhD. Dissertation, The Johns Hopkins University (1982)) and cloned into the SmaI site of M13mp10 in the same orientation with respect to the β-galactosidase α-peptide gene. The EcoR1-HindIII fragment containing the λ DNA sequence was then cut out and cloned into the EcoR1-HindIII site of pLmp10 to yield pLcII. A complete human β-globin cDNA sequence was reconstructed by joining restriction fragments prepared from an incomplete cDNA clone (pJW102- Wilson et al, Nucleic Acids Research 5, 563–581 (1978) and a genomic DNA clone (Lawn et al, Cell 21, 647–651 (1980)) and cloned into the SmaI-HindIII site in M13mp9. M13mp9β cDNA thus obtained was opened at the NcoI site which is located at the initiation codon and treated with Klenow DNA polymerase (Boehringer Mannheim) in the presence of 100 μM 4dNTP to obtain flush ends. The β-globin cDNA sequence was then cut out with HindIII and inserted into the BamHI (filled-in)-HindIII site of pLcII to give the plasmid pLcIIβ, as shown in FIG. 1. In pLcIIβ the β-globin gene is fused to the λCII gene in phase via a small linker DNA derived from M13mp10. In order to construct pLcIIFXβ, M13mp9β cDNA was opened with NcoI and 40 μg of DNA was treated with 200 units of mung bean nuclease (P-L Biochemicals) in 30 mM Na-acetate pH 4.6, 50 mM NaCl, 1 mM $ZnCl_2$, 5% glycerol at 0° C. for 10 minutes to remove the 5' protruding end. The β-globin cDNA sequence was cut out with HindIII and cloned into the StuI-HindIII cut M13mp11FX. The DNA sequence was determined by the dideoxy chain termination method (Sanger et al, PNAS 74, 5463–5467 (1977)) to ensure that the first valine codon of the β-globin gene was preceded by the DNA sequence coding for Ile—Glu—Gly—Arg. Then, the BamHI fragment containing a part of the β-globin sequence was cut out and cloned into BamIII digested pLcIIβ to form pLcIIFXβ as shown in FIG. 1.

c) Expression of λCII/β-globin Hybrid Fusion Proteins in *E coli*

Figure 2:
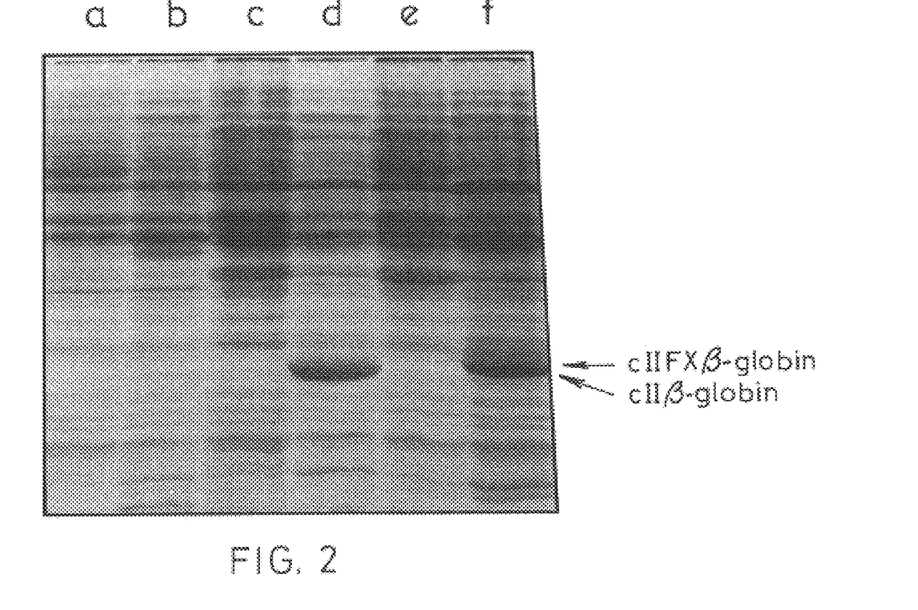
FIG. 2 shows a polyacrylamide SDS gel giving results of fusion protein expression using the vector shown in FIG. 1.

Total cellular proteins from MZ-1 carrying pLcII, pLcIIβ and pLcIIFXβ with and without 2 hour induction were analysed on an 18% polyacrylamide SDS gel and visualised with Coomassie blue. The gel obtained is shown in FIG. 2 in which the lanes are identified by the plasmid carried by the MZ-1 cells as follows:

(a) pLcII at 30° C.;
(b) pLcII at 42° C.;
(c) pLcIIβ at 30° C.;
(d) pLcIIβ at 42° C.;
(e) pLcIIFXβ at 30° C.; and
(f) pLcIIFXβ at 42° C.

METHODS

Figure 3:
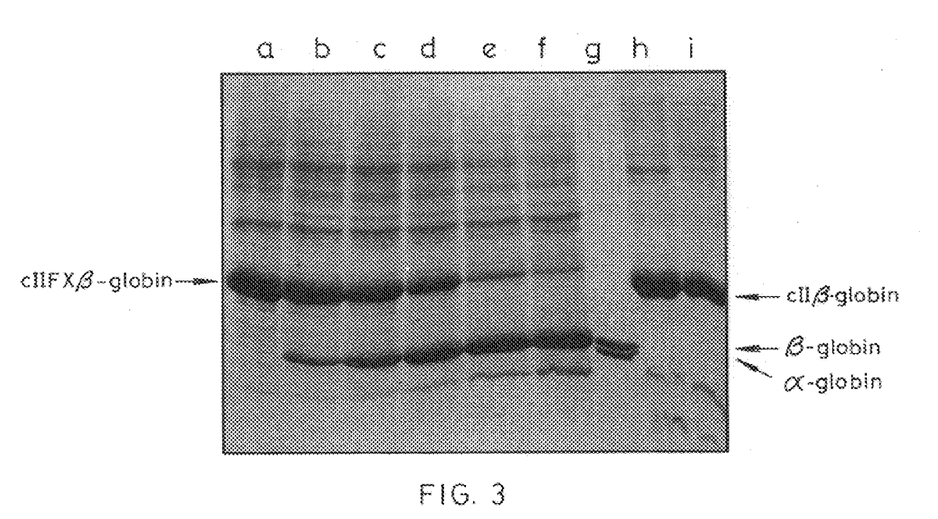
FIG. 3 shows a polyacrylamide SDS gel giving results of cleavage by activated bovine factor $X_a$ of the fusion protein shown in FIG. 2.

MZ-1 harbouring expression plasmids pLcII, pLcIIβ and pLcIIFXβ were grown to $A_{600}$=0.7 in 2×TY medium (Tryptone 16 g, yeast extract 10 g, NaCl 5 g per liter) at 30° C. and the cultures were halved and one half of each culture was mixed with an equal volume of 2×TY which had been preheated to 65° C. and grown at 42° C. The remaining halves were grown at 30° C. as a control. The total cellular protein was extracted with an equal volume of phenol and spun down after precipitation with 5 volumes of ethanol (Remaut et al. supra). The pellets were dissolved in SDS sample buffer and analysed on an 18% polyacrylamide SDS gel as above using the procedure described by Laemmli (Nature 227, 680–685 (1970)).

d) Digestion of CIIFXβ-globin Fusion Protein with Bovine Blood Coagulation factor $X_a$ Samples of CIIFXβ-globin fusion protein were digested with factor $X_a$ at an enzyme to substrate molar ratio of 1:100 at 25° C. for various periods of time and the resultant products were analysed on an 18% poly-acrylamide SDS gel (Laemmli, supra). The gel obtained is shown in FIG. 3, the periods of digestion after factor $X_a$ addition for the various lanes being as follows:

(b) 5 minutes;

(c) 15 minutes;

(d) 30 minutes;

(e) 60 minutes;

(f) 120 minutes

Lane (a) is the result obtained for undigested CIIFXβ-globin and Lane (g) is human adult haemoglobin consisting of the α (faster band) and β (slower band). Also, for the sake of comparison, FIG. 3 contains results for CIIβ-globin fusion protein, which lacks the factor $X_a$ cleavage site, both untreated (Lane (i)) or after 120 minutes treatment with factor $X_a$ as above (Lane (h)). The results show that CIIFXβ-globin is specifically cleaved by factor $X_a$ treatment to give a protein of the same size as authentic human β-globin which accummulates over time and that there is no cleavage of the CIIβ-globin.

METHODS

MZ-1 harbouring pLcIIFXβ was grown in 500 ml 2×TY medium. At $A_{60}$ =0.7, the culture was mixed with 500 ml 2×TY which had been preheated to 65° C. and grown at 42° C. After 2 hours, cells were harvested, and the high salt precipitate was prepared (Gilmer et al, PNAS 79, 2152–2156 (1982)). The pellet was dissolved in 30 ml of 10 mM Na-phosphate pH 6.4, 1% SDS (BDH), 1% β-mercaptoethanol and incubated in a boiling bath for 5 minutes. The sample was dialysed against 10 mM Na-phosphate pH 6.0, 1 mM dithiothreitol, 0.1% SDS and purified on a hydroxylapatite (Bio-Rad, DNA grade) column (Moss et al, J.Biol.Chem.247, 5194–5198 (1972)). The CIIFXβ-globin hybrid protein was concentrated by ultrafiltration (Amicon, PM-10 membrane) and then precipitated with 6 volumes of acetone/0.1 N HCl to remove SDS. The precipitate was air-dried, dissolved in 8 M urea and then dialysed against 100 mM NaCl, 50 mM. Tris-HCl pH 8.0 and 1 mM $CaCl_2$. Bovine blood coagulation factor X (a gift from Dr M P Esnouf) was activated to factor $X_a$ with Russel's viper venom (Sigma) (Fujikawa et al, Biochemistry 11, 4892–4898 (1972)).

EXAMPLE 2

In order to obtain experimental evidence for the narrow substrate specificity of factor $X_a$, a number of proteins were denatured and each was added separately to the CII FX β-globin fusion protein, obtained as set out in Example 1, before digestion with Factor $X_a$. The digestion was carried out as set out in Example 1. The time-course of digestion was then followed by SDS polyacrylamide gel electrophoresis.

In each experiment, ≧70% of the denatured protein substrate remained undigested by the time almost all of the β-globin had been cleaved from the hybrid protein, indicating that each of these polypeptides (>1000 amino acid residues in total) could have been recovered as authentic proteins from hybrid proteins containing a Factor $X_a$ cleavable linker.

METHODS

Bovine serum albumin, human plasminogen, bovine pancreatic trypsin inhibitor and ribounclease A were reduced and alkylated with iodocetic acid in the presence of 5 M guanidine hydrochloride and chicken core histone H2a–H2b dimer was denatured by exposure to 1 M HCl. All six proteins were rapidly digested by trypsin and therefore partly or completely denatured under the conditions used for incubation with CII FX β-globin fusion protein and factor Xa. Each protein was mixed in an equimolar amount of CII FX β-globin fusion protein prepared as set out in Example 1 (c) and digested as set out in Example 1 (d).

EXAMPLE 3

(a) Construction of vector pCT 20210

A vector pCT 20210 was constructed which coded for expression of a chloramphenicol acetyltransferase (CAT) human calcitonin glycine (hCT—Gly) fusion protein containing a factor Xa cleavage sequence (Ile—Glu—Gly—Arg) between the CAT and hCT—Gly polypeptide sequences. As in previous Examples, DNA manipulations were carried out essentially as described by Maniatis et al ('Molecular Cloning', Cold Spring Harbour, N.Y. 1982).

The starting point for construction of the vector pCT 20210 was the vector pCT 2026 which codes for expression of a CATI—Glu—hCT—Gly fusion protein. The construction of vector pCT 2026 is described in detail in GB-A-2 104 810, the disclosure of which is incorporated herein by reference.

Figure 4:
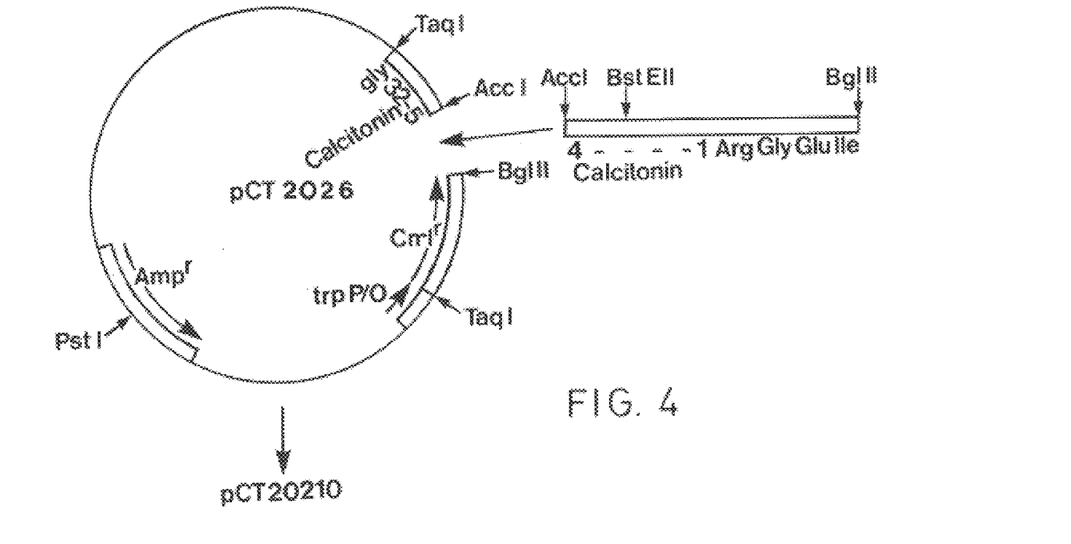
FIG. 4 shows an enzyme restriction map of a vector according to the invention containing a sequence coding for a CAT-Factor Xa cleavage site-human calcitonin-glycine fusion protein.

With reference to FIG. 4, vector pCT 2026 was digested with Acc I and BgI II to excise the DNA sequence coding for Glu and the amino acid residues 1–4 of hCT. The resultant plasmid DNA was isolated and ligated with an excess of the following oligonucleotides:

```
R276
5' - GA TCT ATT GAA GGT CGT TGT GGT AAC CTG T-3'
``` and

```
R275
5' - AGA CAG GTT ACC ACA ACG ACC TTC ATT A-3'
```

The resultant plasmid molecules were transfored into E-coli HB 101 cells and the derived transformed cells selected by growth on media containing ampicillin (100 μg/ml). Transformation and selection was followed by small scale plasmid preparations from the resulting ampicillin resistant colonies and digestion of these DNA molecules with Bst E II. A plasmid containing a Bst E II site, pCT 20210, was isolated and its DNA sequenced in the region of the junction of the sequences coding for the CAT and hCT polypeptides. The DNA sequence determined is shown below together with corresponding amino acid sequence (top line) confirming that pCT 20210 contains the correct sequence coding for the factor Xa cleavage sequence, Ile—Glu—Gly—Arg, between the sequences coding for the CAT and hCT—Gly polypeptides.

(b) Preparation of CAT I Xa hCT Gly fusion protein

E. coli HB101 cells containing plasmid pCT 20210 were cultured at 37° C. to the late exponential phase of growth in a 4 liter fermenter in supplemented mineral salts medium containing 20 μg/ml chloramphenicol. The cells were harvested by centrifugation (1,000 rpm×10 minutes). The cells were resuspended in 60 ml of 50 m Tris HCl buffer, pH 8.0 containing 100 mM NaCl and 1 mM EDTA 0.2 ml of PMSG solution (3.3 mg/ml in ethanol) and 21.4 mg of lysozyme were then added to the suspension. After 25 minutes 2 ml of 4% (w/v) deoxycholate was added and the resultant viscous suspension was left to stand for a further 10 minutes. 0.6 mg of DNase 1 was added and the suspension was left to stand at room temperature until the viscosity had decreased markedly. At completion of this stage the suspension was centrifuged (11,000 rpm×5 minutes), The fusion protein was found to be present predominately in the insoluble pellet fraction.

However some of the CAT—Xa—hCT—Gly fusion protein present in the soluble fraction was purified by CAT substrate affinity chromatography substantially as described for purification of CAT1—Glu—hCT Gly in GB-A-2 104 810.

In addition, the pellet containing the major proportion of the CAT—Xa—hCT—Gly fusion protein was further purified as follows. The pellet was washed with nine volumes of cold, buffered Triton×100 solution (50 mM Tris—HCl, pH 8.0, 10 mM EDTA, 0.55 (v/v) Triton×100, 100 mM NaCl) and recovered by centrifugation (11,000 rpm×5 minutes). This wash procedure was then repeated twice. The resultant pellet was resuspended in 5 ml of the pH 8.0 Tris—HCl suspension buffer as above. The fusion protein was checked for purity by SDS polyacrylamide gel electro-phoresis and the remaining suspension stored at −20° C.

The CAT Xa hCTGly fusion protein purified either from the soluble or insoluble fractions as described above is treated with bovine blood coagulation factor Xa substantially as described in Example 1(c) to yield hCt Gly.

EXAMPLE 4

Chicken myosin light chain cDNA was digested with Sau96, filled-in with Klenow polymerase and cloned into the Stu I site of MP13mp11FX (prepared as set out in Example 1 above) to form M13 mp11FX-MLC. All DNA manipulations were carried out essentially as described by Maniatis et al (loc cit.) . In this M13 derivative, the first amino acid codon of the myosin light chain gene is preceded by a DNA sequence encoding for the Ile—Glu—Gly—Arg tetrapeptide as shown below.

```
                              |Myosin light chain gene
                              |→
GlySerIleGluGlyArgAlaProLysLysAlaLysArgArgAla...
GGATCCATCGAGGGTAGGGCCCCCAAGAAGGCGAAGCGCCGCGCA...
BamHI
```

The myosin light chain cDNA sequence was cut out from M13 mp11FX-MLC together with the factor $X_a$ cleavage sequence and cloned into pLcII to form pLcIIFX-MLC, essentially as described in Example 1.

CIIFX-MLC fusion protein was produced at high level in E. coli and purified to homogeneity. The fusion protein was then cleaved with factor $X_a$ at the peptide bond following the Ile—Glu—Gly—Arg tetra-peptide and the authentic myosin light chain liberated. These manipulations were also carried out essentially as described in Example 1.

The chicken myosin light chain cDNA was obtained as described by Reinach and Fischman, J Mol. Biol., 181 1985.

What we claim is:

1. A fusion product comprising a first DNA sequence coding for an amino acid sequence which is specifically cleaved by blood coagulation Factor $X_a$ and
   a second DNA sequence fused to said first DNA sequence, said second DNA sequence coding for a desired protein or peptide, the second DNA sequence being one which is not naturally fused to said first DNA sequence.

2. The product of claim 1, wherein said first DNA sequence codes for the amino acid sequence X—Y—Gly—Arg wherein X is selected from the group consisting of Ile, Leu, Pro and Ala, and Y is selected from the group consisting of Glu, Asp, Gln and Asn.

3. The product of claim 1, wherein said first DNA sequence codes for the amino acid sequence X—Y—Gly—Arg where X is Ile and Y is selected from the group consisting of Glu and Gln.

4. The product of claim 1, wherein said first DNA sequence codes for the amino acid sequence Ile—Glu—Gly—Arg.

5. The product of claim 1, containing the sequence

ATC GAG GGT AGG.

6. The product of claim 5, containing the sequence

ATC GAG GGT AGG CGT.

7. The product of claim 4, containing the sequence

ATT GAA GGT CGT.

8. A vector comprising a product according to claim 1 inserted therein.

9. A vector selected from the group consisting of M13mp11FX, M13mp11FX-MLC, pLcIIFXβ, pLcIIFX-MLC, and
pCT 20210.

10. The vector of claim 8, wherein said first DNA sequence coding for an amino acid sequence which is specifically cleaved by blood coagulation Factor Xa is also fused to an ATG codon.

11. The vector of claim 8, wherein said first DNA sequence coding for an amino acid sequence which is specifically cleaved by blood coagulation Factor Xa is also fused to a DNA sequence coding for at least part of a host protein.

12. The vector of claim 11, wherein the host protein is selected from the group consisting of lacZ, tufB, trpE, trpD, bla, cII and cat.

13. The vector of claim 8, wherein said first DNA sequence coding for an amino acid sequence which is specifically cleaved by blood coagulation Factor Xa is fused to the 5' end of the DNA sequence coding for said desired protein or peptide product.

14. The vector of claim 8, wherein said desired protein or peptide product is selected from the group consisting of an enzyme, a serum protein, a peptide hormone, and a precursor thereof.

15. The vector of claim 14, wherein said desired protein or peptide product is selected from the group consisting of β-globin, calcitonin-glycine, and myosin light chain.

16. Host cells transformed with a vector according to claim 8.

17. Host cells transformed with a vector according to claim 9.

18. A process, for the production of a desired protein or peptide product in native form, comprising:
   transforming a host cell with a vector according to claim 8;
   expressing the desired protein or peptide product as a fusion protein comprising the desired protein or peptide product fused to the amino acid sequence which is specifically cleaved by blood coagulation Factor Xa; and
   cleaving the fusion protein with Factor Xa to yield the desired protein or peptide product in native form.

19. The process of claim 18, wherein the Factor Xa is prepared by activating Factor X.

20. The process of claim 18, wherein the Factor X is bovine Factor $X_1$ or $X_2$.

21. The process of claim 18, wherein the fusion protein further comprises at least a part of a host protein linked to the amino acid sequence which is specifically cleaved by blood coagulation Factor Xa.

22. The process of claim 21, including the step of purifying the fusion protein by use of an affinity chromatography medium specific for the host protein prior to the cleavage step.

23. The product of claim 1, further comprising a third DNA sequence coding for at least part of a host protein, said third DNA sequence fused to said first DNA sequence coding for an amino acid sequence which is specifically cleaved by a blood coagulation Factor Xa.

* * * * *